United States Patent [19]

Plicchi et al.

[11] Patent Number: 4,567,892

[45] Date of Patent: Feb. 4, 1986

[54] IMPLANTABLE CARDIAC PACEMAKER

[76] Inventors: Gianni Plicchi, 77/7 Via Mascarella; Giancarlo Canducci, 27, Via Cesare Pavese, both of Bologna, Italy

[21] Appl. No.: 474,241

[22] Filed: Mar. 10, 1983

[30] Foreign Application Priority Data

Mar. 16, 1982 [IT] Italy ................................. 3369 A/82

[51] Int. Cl.[4] .............................................. A61N 1/36
[52] U.S. Cl. ............................................. 128/419 PG
[58] Field of Search ................ 128/723, 419 PG, 693, 128/734

[56] References Cited

U.S. PATENT DOCUMENTS

| 3,593,718 | 7/1971 | Krasner et al. | 128/419 PG |
| 3,802,419 | 4/1974 | Yates | 128/723 |
| 4,267,843 | 5/1981 | McDonald et al. | 128/419 PG |
| 4,310,000 | 1/1982 | Lindemans | 128/419 PG |
| 4,344,437 | 8/1982 | Markowitz | 128/419 PG |
| 4,428,378 | 1/1984 | Anderson et al. | 128/419 PG |
| 4,466,440 | 8/1984 | Money et al. | 128/419 PG |

FOREIGN PATENT DOCUMENTS 683722 9/1979 U.S.S.R. ....................... 128/419 PG

OTHER PUBLICATIONS

Barker et al., "Medical & Biological Engineering", vol. 11, No. 3, May 1973, pp. 352-353.

Primary Examiner—William E. Kamm
Attorney, Agent, or Firm—Spencer & Frank

[57] ABSTRACT

An implantable cardiac pacemaker in which the stimulation rate is determined through a suitable programmable algorithm by the patient's ventilation rate which is taken by measuring the impedance variations throughout a distance within the human body; preferably a distance within the thoracic region that goes between the pacemaker box and the lead which is placed subcutaneously. The pacemaker is constructed to detect variations, even rapid ones, of the corporeal impedance and to discriminate substantial variations attributable in all probability to a respiratory act, as well as to limit the drain of electrical energy.

27 Claims, 12 Drawing Figures

IMPLANTABLE CARDIAC PACEMAKER

BACKGROUND OF THE INVENTION

This invention concerns the type of artificial cardiac pacemaker's to be implanted in the patient's body.

At the present state of knowledge, the artificial substitution of mechanisms of generation and conduction of the electrical signals which drive the contractions of the heart depend upon a vast range of artificial pacemakers which are identifiable by initials, accepted through an international agreement, according to the different conditions of action and interaction with the spontaneous activity of the heart. The term "pacemaker" will substitute "artificial cardiac pacemaker" for the rest of this description, keeping in consideration that the above mentioned term is a registered trade-mark. The kind of pacemaker in which the ventricle's stimulation activity is driven and synchronized by the detection of the spontaneous bio-electrical atrial activity are commonly defined as physiological since the electrical impulses that effect the rate are not fixed but induced by the spontaneous atrial rate and are therefore always proportional to it. This kind of pacemaker can only be used in the cases in which the atrial activity can occur in a physiological manner and, therefore, it is only possible in 30 to 60% of the actual pacemaker wearer patients.

Thus, at present, there is a high percentage of patients needing artificial cardiac stimulation that cannot make use of a physiologically variable rate stimulation with the above mentioned technique.

It is for this reason that individuals specialized in this field have been trying for some time to achieve an implantable pacemaker that can respond to a parameter, which instead of the atrial activity parameter, can vary in relation to the physiological needs of the patient, and can be used as a reference variable for automatic and physiological regulation of the electrical impulses that effect the heart rate.

As of today, the pacemakers studied in order to solve the above mentioned problem are those we will describe below in which the stimulation rate is subject, by means of a specific algorithm, to the variations of the following functions:

the hematic PH;
the body temperature;
the quantity of oxygen contained in the blood;
the QT interval observed in an endocardial EKG;
the respiratory rate.

These methods have all had insufficient success due to the complexity and difficulty the pacemaker has in detecting the above mentioned physiological variations. The limits and faults of the above mentioned methods can be summarized in a more specific manner as will follow. As for the pacemaker with control of the hematic Ph, in addition to having the essential problem of safety and reliability which arises with any sensor that is inserted directly into the hematic flow, it was also observed that the sensor decays in too brief a period with respect to the average life of a pacemaker. As for the pacemaker controlled by the amount of $O_2$ in the venous blood there remains the essential problem of reliability and the complexity of a lead which is inserted in the hematic flow and should function both as stimulator and oxygen sensor. Doubts and hesitations must also arise regarding the co-relation between the oxymetric parameter and the heart rate since it has not yet been thoroughly defined. As for the temperature controlled pacemaker, one must remember the limits resulting from the sensor as well as the impossibility, already proven by physiological research, of the body temperature to increase with a time constant similar to that of the heart rate during the patient's physical exercise. As for the QT controlled pacemaker, evident obstacles are found in the difficulty of detecting this data and in the possibility of other causes, deriving for instance from medical therapies of natural physiological evolution, that can determine variations in the QT parameter independently of the potential variations of the heart rate. The hypothesis, which remained such, of pacemakers sensitive to the ventilation rate was based on the detection of this parameter by means of a distorsion transducer placed in an intercostal or interdiaphragmatic area or by means of acoustic transducers placed in an intra-pleural area. Besides the difficulties presented in distinguishing the respiratory signal from that of other functions thus causing it to be unreliable, there would also be the problem of needing a specific surgical approach for setting the said sensors. Another well known attempt, described by an U.S. Pat. No. 3,593,718 is the pacemaker (external, and not implantable) driven by the ventilation rate in which the said function is detected by means of an impedance voltage converter that measures thoracic impedance variations by means of electrodes on the skin of the patient when the ventilation rate changes. The signal coming from this converter is sent directly to a continuous rate/current converter that drives an oscillator that supplies the impulses needed to send the electrical stimulation necessary for the heart, by means of a constant current source at a rate which varies automatically in relation to the ventilation rate. Such a device is impossible to achieve in practice since it lacks a unit capable of converting the voltage into rate and should operate between the first and the second converters just mentioned.

Such a unit would certainly be useless if the output signal from the first converter were to be of the sinusoidal type or perfectly repetitive but it becomes absolutely necessary, presenting quite a few problems in its realization, when one deals with physiological signals that are continuously variable both in width and periodicity, and with continuous variations of the basic line, due to continuous morphological changes and overlapping of false signals. In the U.S. patent mentioned above another difficult task, that is the problem of controlling the energy drain of the entire device, so as to be able to implant it, is not taken into consideration. As a result, one can confirm that the methods proposed up to now have not enabled the various theories to result in an easy to use, totally implantable an reliable product.

SUMMARY OF THE INVENTION

This invention proposes an implantable cardiac pacemaker in which the inhibition rate and/or the stimulation is regulated by the patient's ventilation rate which is detected by analyzing the impedance variations verified due to and accompanying the respiration itself within a specific distance in the human body running from the implanted pacemaker case to a reference lead which is to be inserted preferably subcutaneously in the thoracic area and at a suitable but not critical distance from the said pacemaker.

In the many kinds of pacemakers and in all the different ways in which one must or can stimulate either the atrial or the ventricle or both, it is necessary to fix a minimum inhibition rate and a stimulation rate that does not necessarily coincide with the preceding but can be superior in the pacemakers with hysteresis, which are in any case less frequent. The said rate, called the reference rate, will be fixed by the constructor or programmed in programmable pacemakers at the minimum values which will coincide with the patient's heart beat when in a state of complete rest, normally at 70 beats per minute. As a consequence there is no pacemaker that can comply with a patient's needs when the said patient is carrying out a physical activity requiring a different reference heart rate from the one that was set when the patient was at rest. The new method proposed by this invention will be able to transform the atrial or ventricular inhibition rate from a fixed parameter (more or less programmable) into a parameter that will automatically vary with the metabolic needs of the patient. A pacemaker, when improved according to the new discoveries, will constantly detect the patient's necessary optimal heart rate and will therefore act accordingly.

It became necessary to solve various problems in order to put into practice a pacemaker improved according to the afore mentioned intentions.

The first and probably the most important of such problems was to analyze the impedance variations of the human body with the minimum electrical energy drain since the entire device was destined to be implanted and to supply an electrical cell and it has to have an average independent life of 4–5 years. In order to solve this problem the circuit that detects impedance variations in the human body is supplied with current impulses that are at a higher rate than those of the ventilation rate with the necessary intensity but of very short duration; for instance, impulses in which the relation between the width of each pulse and its period of repetition is approximately 1 to 1000. Programmable amplifiers in which it is possible to program the current drain are used in the circuit of such a pacemaker. Since the best features of these amplifiers such as slew rate and band width are obtained through a high current consumption the amplifiers receive the maximum supply during the phase in which the impulse detects the thoracic impedance variations, that is only at the moment when the amplifying signal is present. Another problem that had to be solved was how to pick up the ventilation rate from the output impedance signal that is noisy and whose amplitude and period vary continuously.

A further problem that had to be solved was regarding the automatic correction of the basic impedance, or rather finding a system that will not be influenced by the basic impedance variations, this being an essential condition of any device which is to be implanted and therefore inaccessible for repair or calibration. To this purpose it is important to keep in mind that the leads that detect the thoracic impedance variations present a basic impedance that is very different from case to case due to the difference between patients and the differences that arise in a patient through time.

A yet further problem to solve was that of realizing a highly reliable, simple, compact device that could easily be realized into an integrated circuit.

These and other problems were solved with the solutions that will seem evident after the following description of the preferred embodiments, illustrated in the annexed four sheets of drawings merely as an example which should not be considered limiting.

DESCRIPTION OF THE PREFERRED EMBODIMENT

Figure 1:
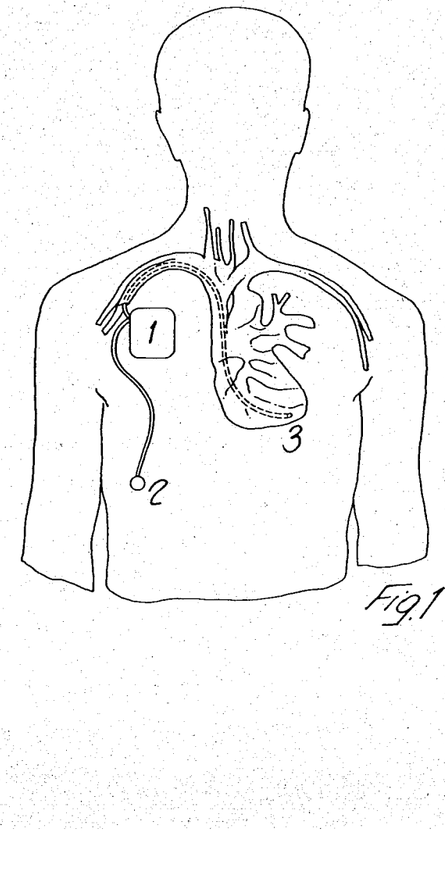
FIG. 1 illustrates how the improved pacemaker is preferably placed in the patient's body.

The improved pacemaker which can be implanted according to the invention is essentially composed of:

a traditional and highly tested electro-stimulating circuit, a circuit that detects thoracic impedance variations and a processor circuit that links the two processing circuits. According to the preferred embodiment of the invention (see FIG. 1), all the electronic components of the pacemaker are placed in container 1 whose surface will act as a common lead for lead 3 which stimulates the heart, as well as lead 2 which detects the thoracic impedance variations. Parts 1 and 2 will be placed in two suitable subcutaneous areas of the thorax, maintaining a proper distance from each other (see FIG. 1). A current impulse of a rate, intensity and width that do not provoke contraction of the underlying muscles is passed between leads 1 and 2 at regular intervals.

The voltage drop of these current impulses on the electrodical body impedance is measured; and from its variations in time the respiration rhythm is obtained. In the block diagram seen in FIG. 2, Z indicates the variable physiological impedance between leads 1 and 2. Unit 10 will pick up the Z impedance variations as measured with current pulses of constant intensity $I_O$.

Figure 2:
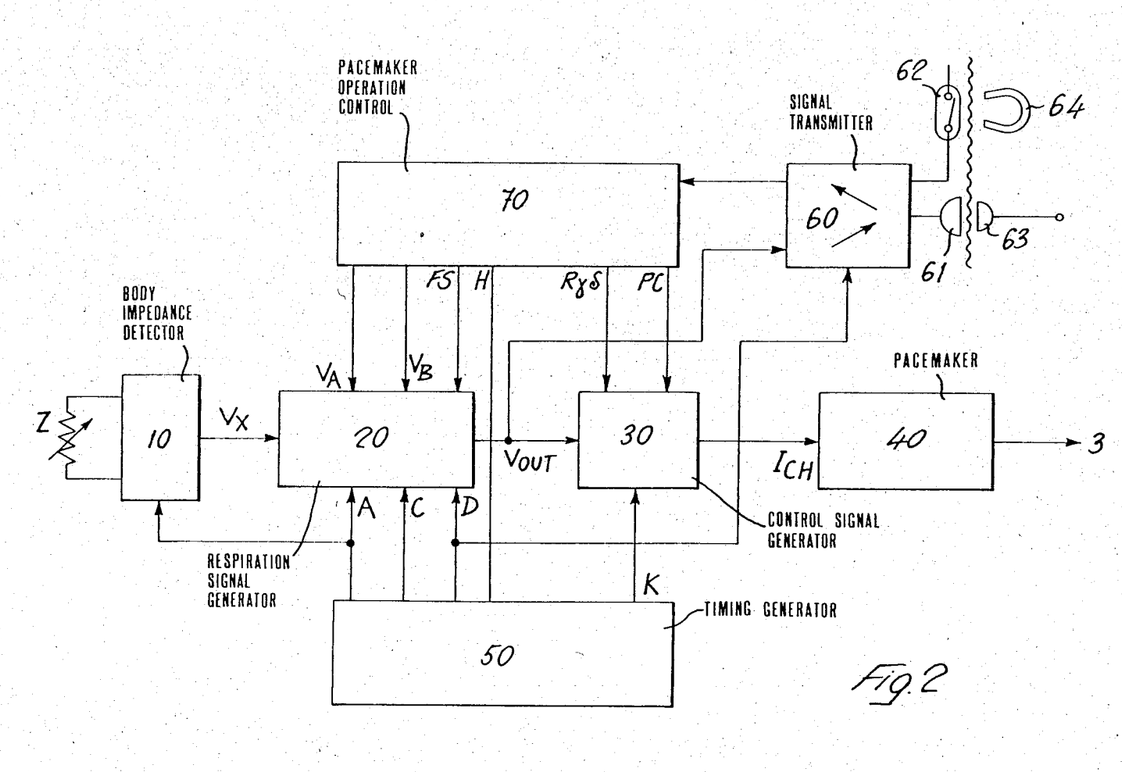
FIG. 2 illustrates a block diagram of the improved pacemaker.

The voltage $I_O \cdot Z$ that exists during each impulse on thoracic impedance is supplied to the subsequent unit 20. This unit is the main innovation of the entire device. In this part the $I_O \cdot Z$ variation is amplified and then compared with threshold levels $V_A$ and $V_B$, the latter is programmable from the outside. After the comparison stage follows a decision stage in which it eliminates errors in detection and discriminates between substantial and less substantial respiratory acts. The unit 20 output is a signal $V_{OUT}$ at logic levels that produces a number of positive transitions equal to the number of substantial respiratory acts.

Unit 30, that follows unit 20, must establish a linear relation, within a field of limited and preestablished values, between the number of positive transitions in the time unit of the said signal $V_{OUT}$ and, for instance, a current $I_{CH}$ charging the capacitor of a normal pacemaker 40 and determining its stimulation rate. In other words, unit 30 realizes the ventilation rate/current conversion so as to allow, along with unit 40, a relation ventilation rate VR/heart rate HR according to the curve chosen and programmed from the curves in FIG. 3 (see further). Number 3 indicates the output from unit 40 that goes to the lead that stimulates the heart. Units 10-20-30 are driven by unit 50 that generates the A-C-D-K timing as will be described further on. The device can transmit information to the outside through unit 60. The $V_{OUT}$ information and the D timing reach this unit. Unit 60 can transmit information regarding the ventilation acts through coil 61 towards the outside and by means of the coil 61 itself, when reed switch 62 is closed, it is able to receive the programming signals coming from coil 63 and to send them to unit 70. Unit 64 is the magnet by means of which it is possible to close read switch 62 when programming the pacemaker. The registers that allow the control of the general working conditions of the entire pacemaker and are protected by a coded identification device are located in unit 70. Included in unit 70 are the means for generating the threshold voltages $V_A$ and $V_B$ and the programming values $R_\gamma$–$R_\delta$–PC along with the H signal that, when sent to unit 50, is responsible for the inhibition of the entire circuit of detection and elaboration of the ventilation rate thus letting the pacemaker work at its fixed reference rate.

Figure 4:
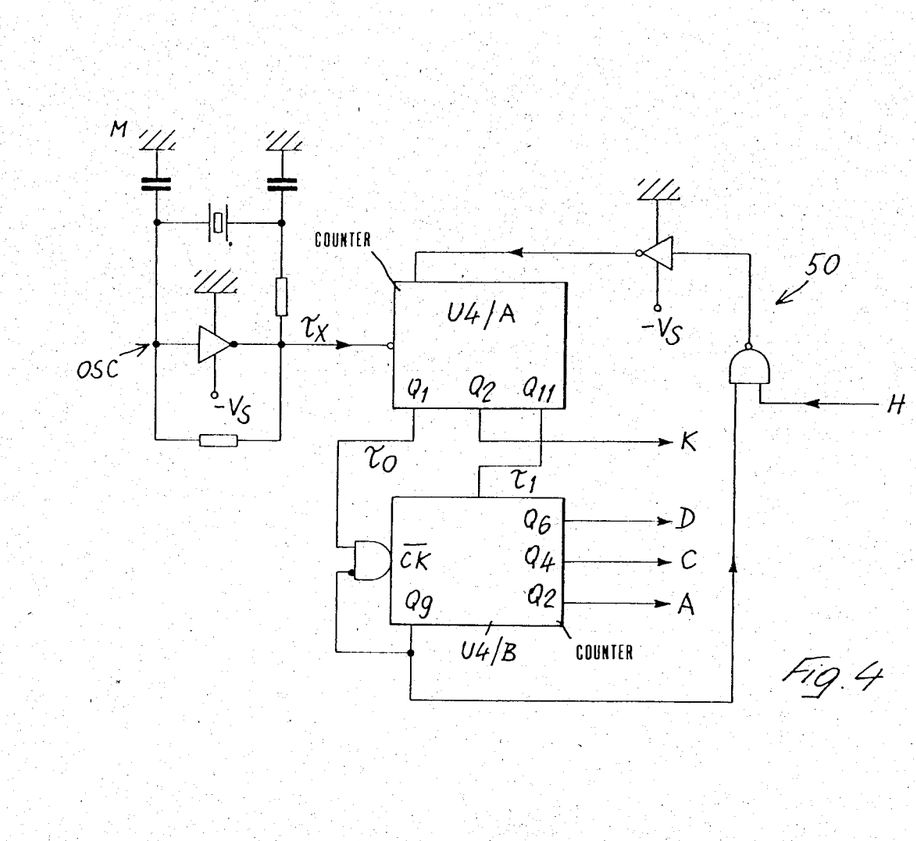
FIG. 4 illustrates with construction details the unit with the timing generator.
Figure 5:
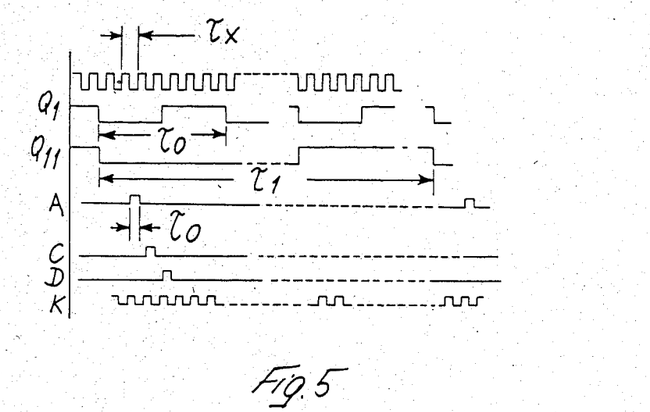
FIG. 5 illustrates the distinctive features of the output signals from the unit of the preceding FIG. 4.

Unit 50 is illustrated in FIg. 4. It includes a twelve stage counter U4/A that fixes the periods $\tau_0$ and $\tau_1$ at circa 120 μsec and 125 msec respectively. This can be seen in FIG. 5 where $\tau_x$ indicates the period of the oscillator OSC that drives the U4/A. Unit 50 also contains a Johnson counter joined to a monostable (Q9 output of U4/B linked to a respective Clock) that creates the necessary phase relationship between signals A-C-D and K. FIG. 5 shows the timing of outputs A-C-D and K when the H input, coming from the external programming stage, is low. When H is high the whole blocks itself and disconnects the detection of the ventilation act (see further). $V_S$ indicates the supply voltage of the pacemaker that is represented by a negative sign since it is normally the positive pole of the battery that is connected to ground M.

Figure 6:
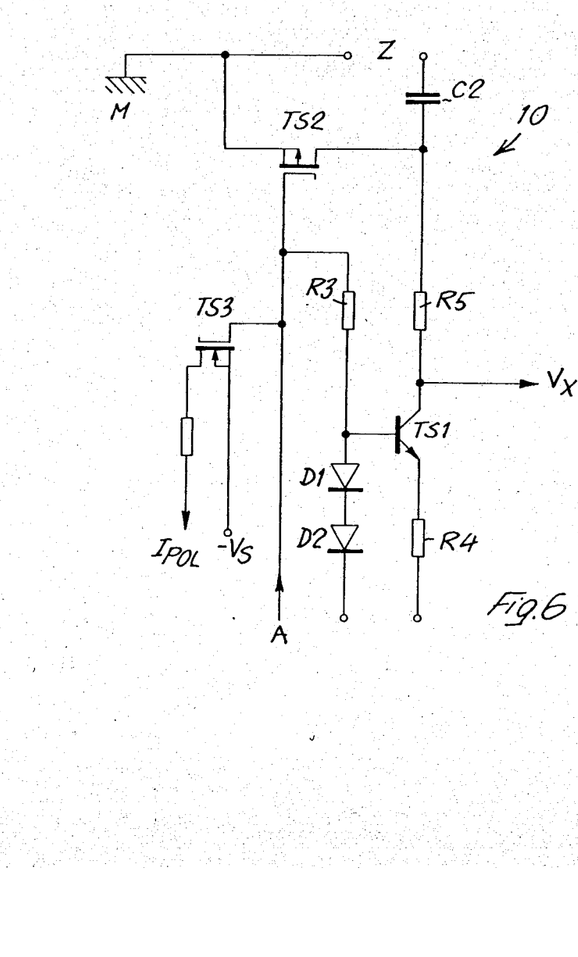
FIG. 6 illustrates the current generator circuit that supplies the leads of the circuit that detects the impedance variations of the human body.

We make reference to FIG. 6 in order to describe the first part of unit 10. A current impulse $I_O$ for instance, of constant intensity, width of 120 μsec, and period of 125 msec, is applied to the physiological load Z that varies during time.

The current $I_O$ generator is made up of TS1-R4-D1-D2-R3 and is driven by signal A with the characteristics as shown in FIG. 5. Since Z is not a totally resistant load, the TS2 switch controlled by A short circuits it when the current generator is off and therefore when A is low. The resistor R5 placed in series with Z and with the decoupling capacitor C2 has the task ot translating the level of the voltage peaks originating from Z in order to bring them to levels which will make them easily manageable by the subsequent components. The TS3 switch is closed when the current impulse $I_O$ is present, that is, when A becomes high and makes the bias current $I_{POL}$ of the operational amplifiers U1/A, U1/B and U1/C (FIG. 7) go from a very low rest value (circa 0,4 μA) to a much higher value (circa 40 μA) in order to assure a fast slew rate of these components during the active phase of measurement of impedance Z and elaboration of the value detected. A voltage $V_X$ formed by very short impulses (see FIG. 8) comes from the circuit in FIG. 6; it varies in amplitude according to the ventilation rate of the patient. This voltage is sent to the circuit in FIG. 7 which has a modified delta modulator containing the components U1/A, U1/C, U2/C, Q3 and the integrator R1-C1. FIG. 8 shows the slope of the main voltage that appear in the circuits taken into consideration here.

In a hypothetical condition with $V_X$ at constant level, the capacitor $C_1$ reaches a voltage $V_C$ slightly superior to the $V_X$ peak. In the circuit mentioned $V_H = A_O \cdot |V_C + V_X|$ where $A_O$ is the gain of the amplifier U1/A and therefore $V_H$ shows a trend of very short impulses. The envelope of the $V_H$ impulse peaks has a $V_A$ average value and profile similar to that of the envelope of $V_X$ peaks. The voltage $V_A$, for example, is chosen with the approximate value of $V_S/2$. When $V_H$ exceeds the threshold $V_A$ a high state of $V_J$ is generated (FIG. 8) and the flip-flop U2/C reset. The output Q3 becomes low and therefore when the buffer Q3, opens there is a slight decrease in the absolute value of $V_C$ which tends to reduce the $V_H$ peak. When the $V_H$ peak does not exceed the $V_A$ threshold the $V_J$ signal remains low and the output Q3 is high since the U2/C bistable was previously set by D. In these conditions, when Q3, opens, the absolute value of $V_C$ increases and it will tend to increase the $V_H$ peak.

If the Z load were to be constant the modulator would alternatively charge and discharge the capacitor $C_1$. Let us now consider Z and therefore $V_X$ as variable values around the average values $Z_M$ and $V_{XO}$ respectively as shown in FIG. 8.

The envelope $V_H$ of the $V_H$ peaks is none other than the $V_X$ envelope multiplyed by $A_O$ and centered on $V_A$. This holds true for rather rapid variations so that $V_C$ will not vary perceptibly. This condition can be obtained by adopting a sufficiently high R1-C1 time constant. This part of the circuit obtains the automatic adjustment of the device to the slow basic impedance variations and a signal $V_J$ indicates when the rapid variations of the Z impedance are of a certain consistency and therefore can be attributed to a possible evolution of a respiratory act.

Figure 7:
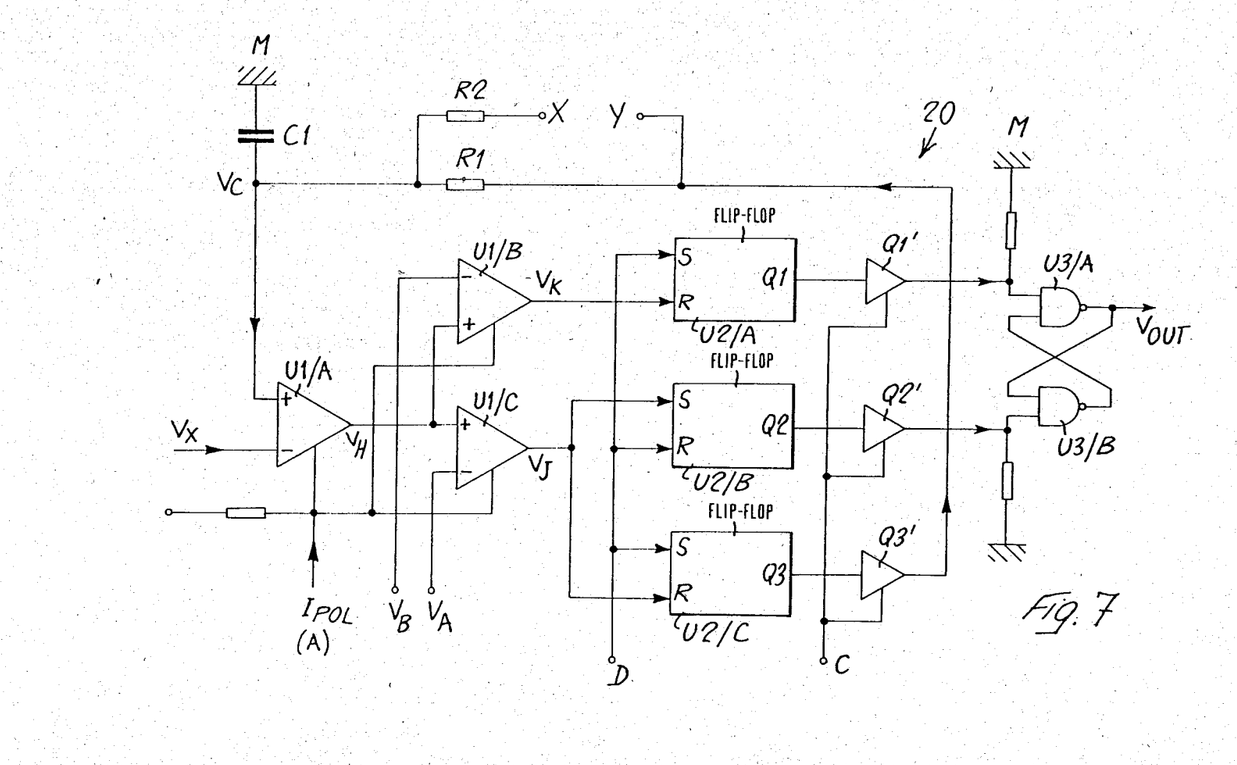
FIG. 7 illustrates the circuit of the unit that elaborates the impedance variations of the human body, which will cause the automatic adjustment of the device to the slow variations of the basic impedance and then detect the ventilation rate.
Figure 8:
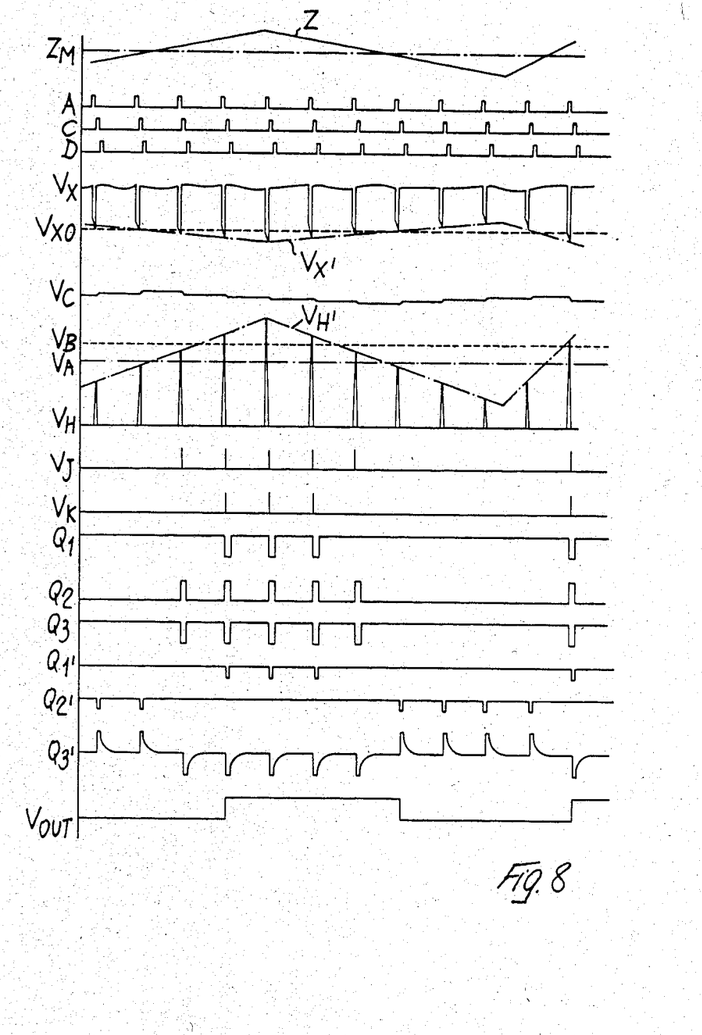
FIG. 8 illustrates the various wave forms of the signals present in the circuits of FIGS. 6 and 7.

FIG. 7 also shows that through the operational amplifier U1/B the signal $V_H$ is also compared with a voltage threshold $V_B$ with a higher value than $V_A$ and therefore the output $V_K$ of U1/B signals the presence of variations of Z superior to the Z threshold value $$= \frac{V_B - V_A}{A_O \cdot I_O}.$$

In the presence of such high variations, $V_K$, by means of U2/A and the buffer Q1' will set the flip-flop composed of U3/A–U3/B. The reset situation of said device can only be reached when the $V_H$ peak goes under the threshold $V_A$ or when, with a high C, there are no positive impulses at the output Q2 of U2/B. The circuit described therefore introduces a sort of hysteresis with a variable width, varying $V_B$ in regards to $V_A$, that has a double aim: eliminate improper transitions due to noise, and create a sensitivity control that can descriminate between more or less consistent variations of the impedance Z. With reference to FIG. 7 note that when the pacemaker is implanted and set, the connections of points X-Y and the resulting connection in parallel of low value R2 resistor to R1, is controlled by the programming circuit from the outside, as will be described further, so that the $V_C$ will rapidly reach the necessary values.

Figure 9:
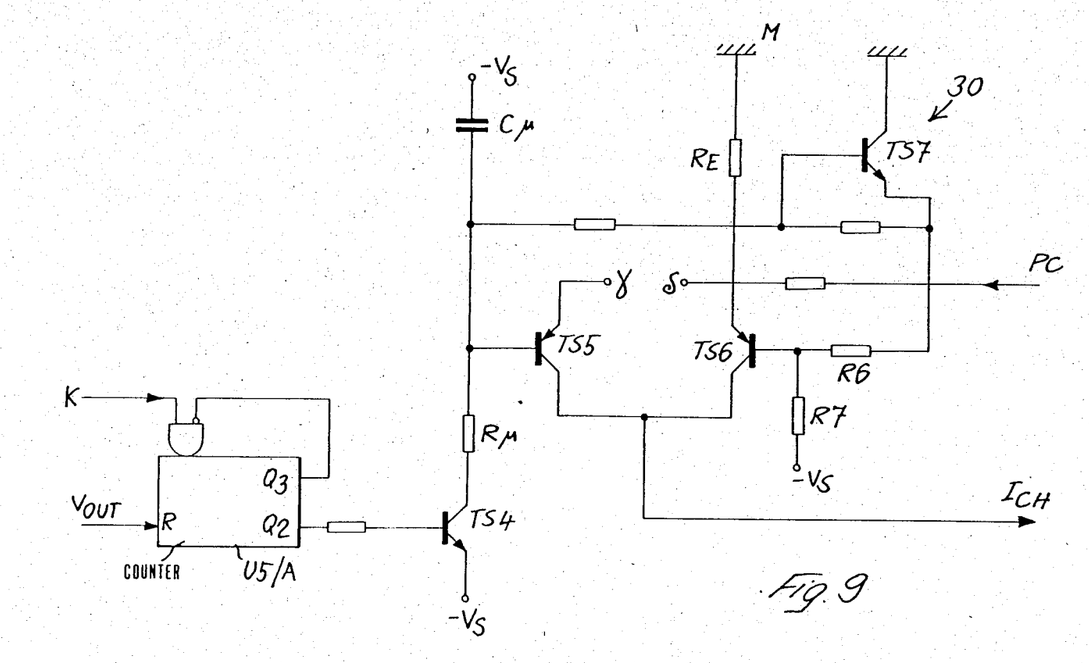
FIG. 9 illustrates the circuit of the unit that establishes the relation between ventilation rate and the current that determines the stimulation rate of a possible pacemaker circuit at the final stage.

The output signal $V_{OUT}$ from the circuit in FIG. 7, as can be seen in FIG. 8, has the same number of positive transitions as the number of respiratory acts and represents the patient's ventilation rate. FIG. 9 illustrates an example of the possible use of the $V_{OUT}$ signal to construct a physiological pacemaker as explained in the introduction of this paper. In unit 30 shown in FIG. 9, the signal $V_{OUT}$ enters in U5/A and becomes correlated to the number of falling edges of the K signal that forms the U5/A clock, the latter is a monostable and for each falling edge of $V_{OUT}$ an impulse of approximately 1 msec is present at the output Q2. The output Q2 drives TS4 that terminates into the Ru-Cu integrator whose average voltage drives the TS5 base. Until the TS5 base voltage remains higher than that of TS6 (reference voltage) the whole current $I_{CH}$ is determined by $R_E$ and by TS6 as well as by the reference voltage generated by TS7 and the R6-R7 divider. In practice, therefore, when the absolute value of the TS5 base voltage increases there are no perceptible $I_{CH}$ variations. An increase of the current $I_{CH}$ occurs when the TS5 and TS6 base voltages become the same. When the TS5 base voltage becomes inferior to the TS6 one, the dependence of the $I_{CH}$ from the TS5 base voltage becomes practically linear. This characteristic depends upon the load inserted between $\gamma$ and $\delta$ and the PC (Constant Programming) state.

Figure 3:
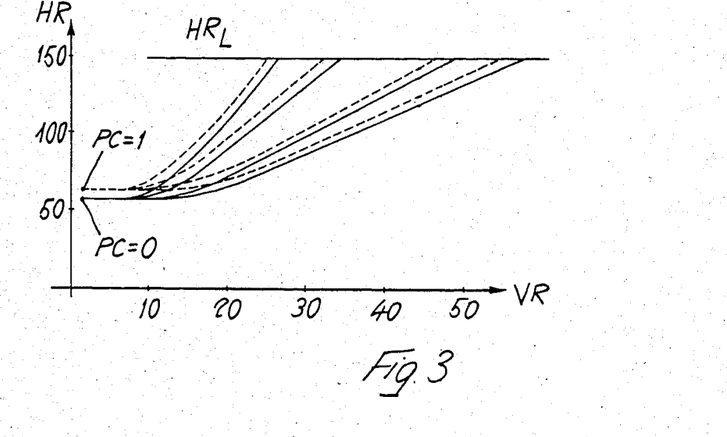
FIG. 3 illustrates the possible curves of the ventilation rate/heart rate relation at which the pacemaker can be programmed.
Figure 10:
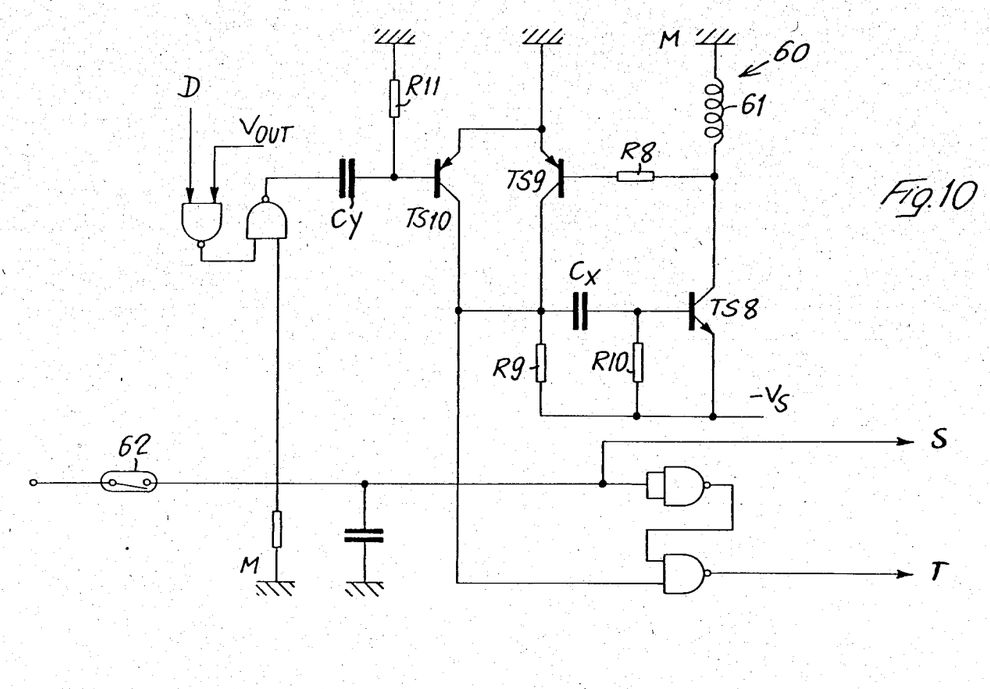
FIG. 10 illustrates the circuit of the unit that enables the dialogue with the outside and to program the pacemaker.

With a high or a low PC it is possible to choose, respectively, either the family of dotted curves, or the one indicated with a solid line in FIG. 3, while by acting on the $\gamma$ and $\delta$ values it is possible to choose the desired curve from the five work curves indicated for each of the said families. The current $I_{CH}$, as already stated when referring on FIG. 2, charges the capacitor of the oscillator of the pacemaker's circuit thus determining a linear stimulation rate (see further). Unit 60, as shown in FIG. 10, allows the communication of the system with the outside. When reed switch 62 is open the information regarding the respiratory act is sent to the outside by a train of 20 μsec pulses with a 125 msec period between each impulse, when $V_{OUT}$ is high. This is obtained by sampling the $V_{OUT}$ signal through signal D and associating, at each falling edge of the sampled signal, a 20 μsec pulse that charges the coil 61.

This impulse is generated by a monostable circuit made up of TS8-TS9 R8-R9-R10-CX and triggered by the TS10-CY-R11. In the condition considered above the outputs S and T are kept high (see further).

With reed switch 62 closed, S goes low, and the transmission is disabled since there is no trigger signal on TS10, while the output T is enabled for reception.

In this condition, each suitable variation of the magnetic flux induced from the outside on coil 61 starts a monostable cycle and there is a 20 μsec impulse on R9. A train of external magnetic impulses with an inferior or equal (20 μsec) duration starts off a similar train of impulses at output T also having a 20 μsec duration. In this situation output S are low. With the re-generative stage, as shown in FIG. 10, it is possible to eliminate improper transitions due to noise and undesired magnetic fields.

Figure 11:
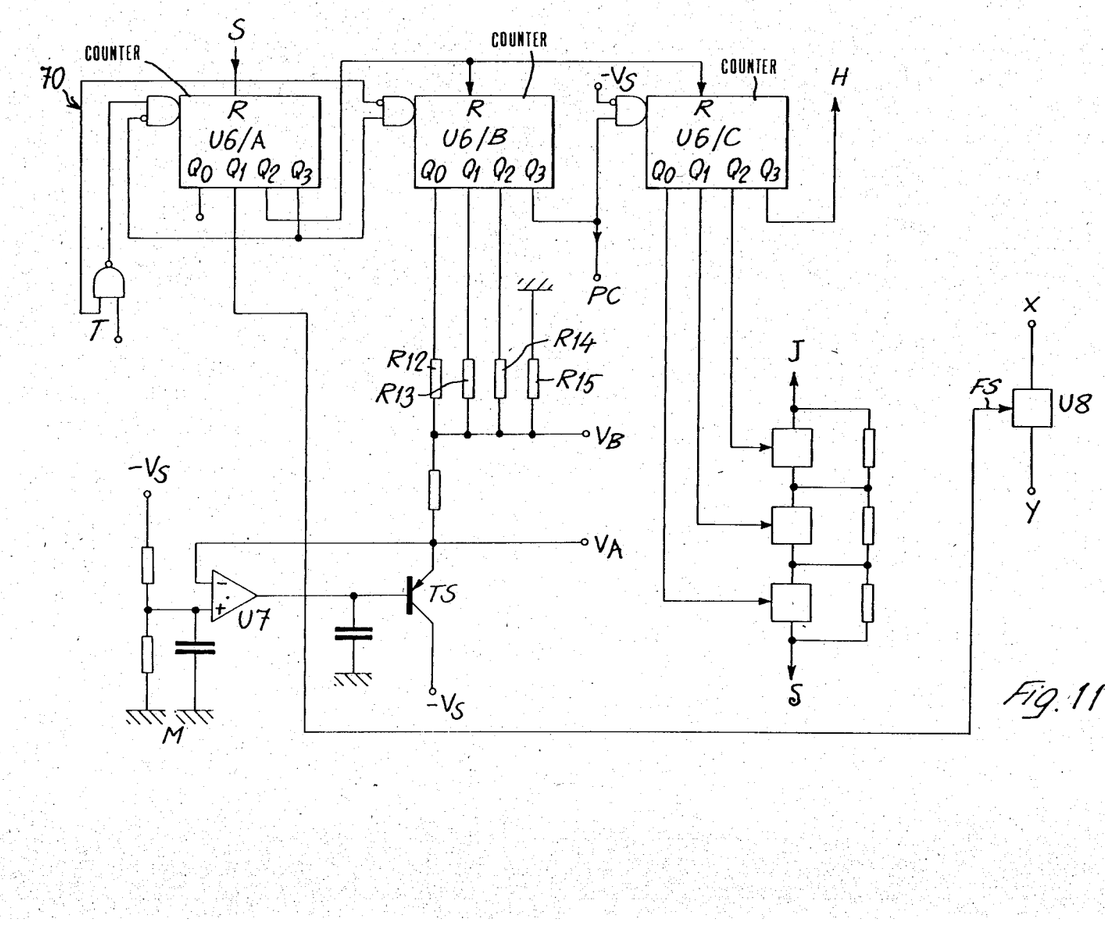
FIG. 11 illustrates the circuit of the registers which be able to determine the global working condition of the pacemaker.

The description of Unit 70 makes reference to FIG. 11. As already observed in FIG. 10, the impulses received from the outside are present in output T while S is low. The circuit in FIG. 11 can set some of the devices parameters through the number of impulses coming from the outside.

This portion of the circuit can generate the voltage $V_A$ which is equal to $V_S/2$ as mentioned before; it can generate the variable $V_B$ threshold value through U7 and TS; it establishes the load between points $\gamma$ and $\delta$ and therefore, along with the output PC, gives the possibility of selecting 16 different operative conditions of stage 30; it can activate the switch located between X and Y creating the FS conditions, a rapid start of the circuit that detects the ventilation rate, and lastly can also exclude this function with a high H. As already mentioned unit 70 includes a protection for the information received. In order to program the pacemaker reed switch 62 must be closed and programming impulses must be preceded by an eight impulse key code. The counter U6/A reads the key-code and activates the FS function by means of U8 when the second key-code impulse is received and Q1 goes high. When the external magnet 64 (FIG. 2) is removed reed switch 62 opens while S goes high and Q1 goes low, this will determine the end of FS. Returning for a moment to U6/A, notice that the output Q3 goes high when the eighth key-code impulse is received and reed switch 62 is closed for programming. The counter U6/A stops and the impulses T are switched to the counters U6/B, U6/C. The number of the impulses which is higher than that of the key-codes, will determine the output state of said U6/B and U6/C combination.

Q0-Q1-Q2 outputs of U6/B unit together with the R12-R13-R14-R15 resistors make up an analogical-digital converter whose output generated VB. The Q3 output of the U6/B unit and the Q0-Q1-Q2 outputs of U6/C unit will determine the specifics of the conversion circuit that generates the current $I_{CH}$ (FIG. 9). Lastly the output Q3 of U6/C can, if chosen, generate the impulse H and therefore disactivate the respiratory act detecting function. While the key-code is transmitted, at the fourth impulse, the Q2 output of the U6/A resets the contents of register U6/B and U6/C. By removing magnet 64, 62 opens and U6/B reset. By re-closing 62 with the external magnet, S goes low and the key register U6/A is ready to accept the code to begin programming once again.

Figure 12:
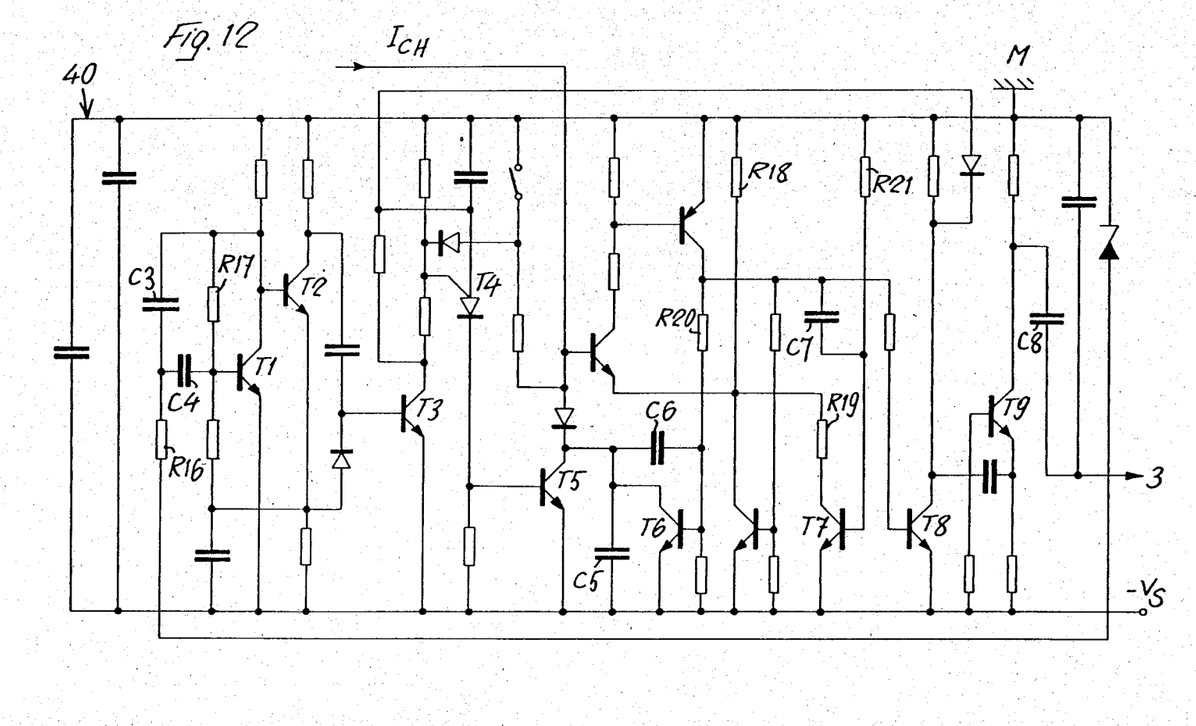
FIG. 12 illustrates a possible realization of the circuit at the final stage of the heart stimulator.

FIG. 12 illustrates unit 40 that, in this example, corresponds to a demand heart pacemaker. Output 3 goes to the heart. The stimulation signals are sent and the EKG signals are received by this terminal. The latter, filtered from R16-C3-C4-R17, is amplified by T1 and T2 and sent to the circuit, made of T3-T4-T5 and relative connected components, that creates the functions that form the refractory period after each stimulation impulse and that reject external interference. Through T5 each EKG signal received discharges the capacitor C5. If heart signals are absent, C5 wil be charged by $I_{CH}$ and when the threshold which is determined by R18-R19 is reached T6 will discharge it in a short time which is determined by C6-R20. This is the width of the stimulation impulse. The impulse rate is therefore controlled by $I_{CH}$-T7-C7-R21 that determines the maximum rate value that can be reached, indicated in FIG. 3 by $HR_L$. The stimulation impulse amplitude is duplicated by T8-T9 and sent to the heart by C8. It is to be understood that the various $V_A$, $V_B$ and other currents were considered in their absolute value without indicating the negative sign that in reality marks them.

It also remains to be understood that the description refers to a possible or rather a preferred solution for the construction of the invention. Numerous variations and modifications can be made, especially in the construction aspect.

According to a variant, other means from those illustrated may be used, linked to the significant part of the circuit that gets the $V_{OUT}$ signal which was described in FIGS. 1, 6, 7, 3 in order to create a pacemaker which will self-adapt to the physiological need of the patient. It then remains to be understood that the Z impedance variation measures can be taken with a constant voltage system rather than with the constant current system. Other variations can be made by using different electronic components from the ones described but they must have the same or similar functions. The device described herein has a limited programming but this does not means that a programmable pacemaker cannot have many more functions by a more extended use of the C-MOS components in the traditional stimulation part and still keep the same qualities of the one discussed here. These and all other modifications which will be evident to the technicians in this field are not beyond the limits of the invention herein described, illustrated and as further claimed.

We claim:

1. A heart pacemaker implantable in a patient, said pacemaker comprising:
    impedance responsive means constructed to be operatively associated with the patient for detecting impedance variations in the patient's body which are at least in part dependent on the act of respiration and for deriving an impedance signal corresponding in value to such impedance variations;
    signal extraction means connected to said impedance responsive means for deriving from the impedance signal a respiration dependent signal which undergoes a variation in value each time the value of the impedance signal exceeds a selected threshold value, whereby the respiration dependent signal is a periodic signal synchronized with respiration acts of the patient;
    programmable signal generating means connected to said signal extraction means for deriving from the respiration dependent signal a stimulation control signal which is linearly proportional to the respiratory rate of the patient, between selected upper and lower limits;
    heart stimulation means connected to said signal generating means for supplying stimulation signals to the patient's heart at a rate controlled by the stimulation control signal; and
    programming means operatively associated with said signal extraction means for adjusting the selected threshold value under control of programming signals delivered from outside the patient's body.

2. A pacemaker as defined in claim 1 wherein:
    said heart stimulation means include at least one implantable electrode for applying the stimulation pulses to the patient's heart; and
    said impedance responsive means comprise two measuring electrodes one of which is conductively connected to said at least one implantable electrode and the other of which is insertable subcutaneously at a selected distance from said one measuring lead.

3. A pacemaker as defined in claim 2 further comprising an external case having an electrically conductive outer surface constituting said one measuring electrode.

4. A pacemaker as defined in claim 1 wherein said impedance responsive means are operative for monitoring the impedance between two selected points of the patient's body in response to application of an electrical signal having a selected intensity between those points, and said impedance responsive means comprise: two measuring electrodes installable at the selected points; and means connected to apply between said electrodes a succession of pulses of the electrical signal having the selected intensity, the pulses being of short duration and the succession of pulses having a high ratio of pulse repetition period to pulse duration, whereby the impedance is monitored at regular intervals with low energy consumption.

5. A pacemaker as defined in claim 4 wherein the electrical signal is a current and said means for applying a succession of pulses comprise a current generator connected to be actuated by a short duration signal triggering each electrical signal pulse, and to be turned off between pulses to minimize energy consumption.

6. A pacemaker as defined in claim 5 wherein the ratio of pulse repetition period to pulse duration is of the order of 1000 to 1.

7. A pacemaker as defined in claim 5 further comprising a supply voltage source, and wherein said signal extraction means comprise: a first amplifier having first and second inputs and an output and having its first input connected to receive the impedance signal derived by said impedance responsive means; a first comparator having a first input connected to said first amplifier output, a second input connected to receive a first reference voltage substantially equal to one-half the supply voltage, and an output supplying a signal each time the value of the signal at said first input exceeds the value of the signal of said second input; a first flip-flop having a set input, a reset input and an output, with said reset input being connected to said output of said first comparator; a source of a first control signal corresponding to the short duration signal triggering each electrical signal pulse, said source being connected for applying said first control signal to said set input of said first flip-flop; and means including an RC network connecting said output of said first flip-flop to said second input of said first amplifier; wherein the voltage, $V_H$, at the output of said first amplifier has a value:

$$A_o|V_c - V_x|, \text{ where}$$

$A_o$ is the gain of said first amplifier, $V_x$ is the voltage of the signal at said first input of said first amplifier, and $V_c$ is the voltage of the signal at said second input of said first amplifier, and wherein the time constant of said RC network is sufficiently long to adapt $V_c$ to long term variations of the patient's body impedance detected by said impedance responsive means.

8. A pacemaker as defined in claim 7 wherein said signal extraction means comprise a modified delta modulator containing said first amplifier.

9. A pacemaker as defined in claim 8 wherein said signal extraction means further comprise a second comparator having a first input connected to said first amplifier output, a second input connected to receive a second reference voltage having a value greater than said first reference voltage and constituting the selected threshold value, and an output supplying a signal each time the value of the signal at said first input of said second comparator exceeds the value of the signal at said second input of said second comparator, wherein said first and second comparators constitute a sensitivity control circuit for discriminating between consistent and inconsistent body impedance variations detected by said impedance responsive means.

10. A pacemaker as defined in claim 9 wherein the values of the first and second reference voltages are programmable by said programming means and said first amplifier and said comparators are connected to receive operating power during short periods when the impedance signal is being produced in response to each current pulse.

11. A pacemaker as defined in claim 9 wherein said first comparator comprises means for producing a signal pulse each time a signal appears at said output of said first comparator, said second comparator comprises means for producing a signal pulse each time a signal appears at said output of said second comparator, and said signal extraction means further comprises a third comparator connected to receive the signal pulses produced by said signal pulse producing means of said first and second comparators, said third comparator having an output which provides a signal constituting the respiration dependent signal which undergoes such variation in value in response to a first signal pulse from said signal pulse producing means of said second comparator and until passage of a selected time interval during which no signal pulse is produced by said signal pulse producing means of said first comparator.

12. A pacemaker as defined in claim 11 wherein: said RC network comprises a compacitor and a first resistor which together establish the sufficiently long time constant; said network further comprises a second resistor having a lower resistance than said first resistor; and said programming means are operative for selectively and temporarily connecting said second resistor in parallel with said first resistor at the start of operation of said pacemaker for rapidly adapting the response of said signal extraction means to the value of the body impedance the variations of which are being detected.

13. A pacemaker as defined in claim 4 wherein said impedance responsive means further comprise: control signal generating means connected for applying to said current generator the short duration control signal triggering each electrical signal pulse; and circuit means connected between said measuring electrodes and controlled by the short duration control signal for establishing a short circuit between said measuring electrodes during the intervals between the electrical signal pulses in order to prevent difficulties resulting from the fact that the impedance between the two selected points of the patient's body is not purely resistive.

14. A pacemaker as defined in claim 1 wherein the stimulation control signal produced by said programmable signal generating means establishes a selected linear relation between the respiration rate indicated by the respiration dependent signal and a selected function controlled by the signals produced by said heart stimulation means.

15. A pacemaker as defined in claim 14 wherein the selected function is inhibition rate.

16. A pacemaker as defined in claim 14 wherein the selected function is atrial stimulation rate.

17. A pacemaker as defined in claim 14 wherein the selected function is ventricular stimulation rate.

18. A pacemaker as defined in claim 1 wherein said programming means comprise means for transmitting to a location outside of the patient's body signals representative of respiration acts and means for transmitting from the location outside of the patient's body to said signal extraction means and said programmable signal generating means control signals for controlling the sensitivity of said signal extraction means to the intensity of respiration and for controlling the relation between the respiration dependent signal and at least one of inhibition rate and heart stimulation rate.

19. A pacemaker as defined in claim 18 wherein said programming means comprise means for transmitting from the location outside of the patient's body a selected coded signal, and implantable receiving means responsive to the coded signal for temporarily shortening the time constant of said RC network at the start of operation of said pacemaker.

20. A pacemaker as defined in claim 19 wherein said means for transmitting further constitute a source of a first setting signal representing the desired magnitude of the selected threshold value and a second setting signal representing the desired proportional relation between the stimulation control signal and the respiration rate indicated by the respiration dependent signal, and said receiving means are operative for adjusting the selected threshold value in dependence on the first setting signal and for adjusting the relation between the stimulation control signal and the respiration dependent signal in dependence on the second setting signal.

21. A pacemaker as defined in claim 20 wherein said means for transmitting further constitute a source of a third setting signal, and said receiving means are further operative for responding to occurrence of the third setting signal for causing said heart stimulation means to supply stimulating signals at a selected rate independent of the respiration dependent signal.

22. A pacemaker as defined in claim 1 further comprising means connected for preventing the rate of the stimulation signals produced by said heart stimulation means from passing beyond selected upper and lower limits independently of the rate of the patient's respiration acts.

23. In a heart pacemaker implantable in a patient, the pacemaker comprising:

impedance responsive means constructed to be operatively associated with the patient for detecting impedance variations in the patient's body which are at least in part dependent on the act of respiration and for deriving an impedance signal corresponding in value to such impedance variations, and heart stimulation means connected to the impedance responsive means for supplying stimulation signals to the patient's heart at a rate controlled by the impedance signal, the improvement wherein said impedance responsive means are operative for monitoring the impedance between two selected points of the patient's body in response to application of an electrical signal having a selected intensity between those points, and said impedance responsive means comprise: two measuring electrodes installable at the selected points; and means connected to apply between said electrodes a succession of pulses of the electrical signal having the selected intensity, the pulses being of short duration and the succession of pulses having a high ratio of pulse repetition period to pulse duration, whereby the impedance is monitored at regular intervals with low energy consumption.

24. A pacemaker as defined in claim 23 wherein the electrical signal is a current and said means for applying a succession of pulses comprise a current generator connected to be actuated by a short duration signal triggering each electrical signal pulse, and to be turned off between pulses to minimize energy consumption.

25. A pacemaker as defined in claim 24 wherein the ratio of pulse repetition period to pulse duration is of the order of 1000 to 1.

26. A pacemaker as defined in claim 23 wherein said impedance responsive means further comprise: control signal generating means connected for applying to said current generator the short duration control signal triggering each electrical signal pulse; and circuit means connected between said measuring electrodes and controlled by the short duration control signal for establishing a short circuit between said measuring electrodes during the intervals between the electrical signal pulses in order to prevent difficulties resulting from the fact that impedance between the two selected points of the patient's body is not purely resistive.

27. In a heart pacemaker implantable in a patient, the pacemaker comprising:

detecting means constructed to be operatively associated with the patient for detecting variations in a parameter of the patient's body and for deriving a signal corresponding in value to such variations, and heart stimulation means connected to the detecting means for supplying stimulation signals to the patient's heart at a rate controlled by the signal, the improvement wherein said detecting means are operative for monitoring the parameter between two selected points of the patient's body in response to application of an electrical signal having a selected intensity between those points, and said detecting means comprise: two measuring electrodes installable at the selected points; and means connected to apply between said electrodes a succession of pulses of the electrical signal having the selected intensity, the pulses being of short duration and the succession of pulses having a high ratio of pulse repetition period to pulse duration, whereby the parameter is monitored at regular intervals with low energy consumption.

* * * * *